United States Patent [19]
Sim et al.

[11] Patent Number: 5,591,881
[45] Date of Patent: Jan. 7, 1997

[54] STEREOSELECTIVE PREPARATION OF (E)-ENOLTHIOETHER DERIVATIVES

[75] Inventors: Young-Ki Sim; Tae-Seop Hwang, both of Kyungki-do; Mi-Jung Lee, Kyungsang-buk-do; Hee-An Kwon; Tea-Heung Song, both of Kyungki-do, all of Rep. of Korea

[73] Assignee: Choongwae Pharmaceutical Co., Ltd., Seoul, Rep. of Korea

[21] Appl. No.: 512,507

[22] Filed: Aug. 8, 1995

[30] Foreign Application Priority Data

Aug. 10, 1994 [KR] Rep. of Korea .................. 94-19644

[51] Int. Cl.$^6$ ................................................ C07F 7/08
[52] U.S. Cl. ............................................................. 556/427
[58] Field of Search ............................................... 556/427

[56] References Cited

U.S. PATENT DOCUMENTS

| | | | |
|---|---|---|---|
| 4,816,581 | 3/1989 | Schmid | 540/359 |
| 5,187,305 | 2/1993 | Thompson et al. | 556/427 X |
| 5,237,083 | 4/1993 | Martino et al. | 556/427 X |

FOREIGN PATENT DOCUMENTS 0179318  10/1985  European Pat. Off. .

OTHER PUBLICATIONS

M. Ishiguro et al., "Studies on Penem Antibiotics", *The Journal of Antibiotics*, vol. XLI, No. 11, Nov. 1988, pp. 1685–1693.

R. Tanaka et al., "Synthesis of 5,6–cis–Penems", *The Journal of Antibiotics*, vol. XLIII, No. 12, Dec. 1990, pp. 1608–1610.

S. Takano et al., "A Stereoselective Route to E–3–Hydroxyalkenyl Phenyl Sulfides", *Tetrahedron Letters*, vol. 34,, No. 5, pp. 845–846, 1993, pp. 845–846.

T. Nakatsuka et al., "A Facile Conversion of the Phenylthio Group to Acetoxy by Copper Reagents for a Practical Synthesis of 4–Acetoxyazetidin–2–one Derivatives from (R)–Butane–1,3–diol", *J. Chem. Soc., Chem. Commun.*, 1991, pp. 662–664.

*Primary Examiner*—Paul F. Shaver
*Attorney, Agent, or Firm*—Gary M. Nath; Nath & Associates

[57] ABSTRACT

A process for stereoselective preparation of (E)-enolthioether derivatives comprising the steps of;
(a) protecting free secondary hydroxy group of L-threonine with trialkylsilyl group; (b) the protected L-threonine derivatives (I) being degraded by ninhydrin to prepare (2R)-2-(trialkylsilyloxy)propanal (II); and (c) carting out the Honor-Wordsworth-Emons (HWE) reaction of the resultant compound (II) with stabilized phosphonate ylide, phosphonium ylide or phosphine oxide ylide which was obtained by treating the organic phosphine compound (III) with strong base to provide (E)-enolthioether derivatives (IV) is provided.

The present invention has advantages in comparison with the prior art in that the costs required for the process can be lowered because L-threonine, an α-amino acid of low in price is used as a starting material and the process is simple; and the desired (E)-enolthioether derivatives can be prepared with high stereoselectivity.

10 Claims, No Drawings

STEREOSELECTIVE PREPARATION OF (E)-ENOLTHIOETHER DERIVATIVES

FIELD OF THE INVENTION

The present invention relates to a stereoselective preparation of (E)-enolthioether derivatives represented by the following formula (IV);

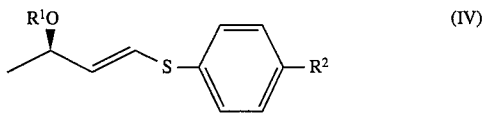

wherein, $R^1$ is a trialkylsilyl group; $R^2$ is a hydrogen; $C_{1-3}$ lower alkyl, $C_{1-3}$ lower alkoxy or halogen atom, especially chlorine atom; through so-called Honor-Wordsworth-Emons reaction (hereinafter, abbreviated as "HWE reaction") starting from L-threonine, α-amino acid plentiful in the nature.

4-Acetoxyazetidinone derivatives represented by the following formula (a), 4-phenylthioazetidinone derivatives represented by the following formula (b) and 4-phenylsulfonazetidinone derivatives represented by the following formula (c) as intermediate compounds for the manufacture of beta-lactam antibiotics of carbaphenem- or phenem-type having a potent antibiotic activity can be synthesized through the (E)-enolthioether derivatives of the said formula (IV):

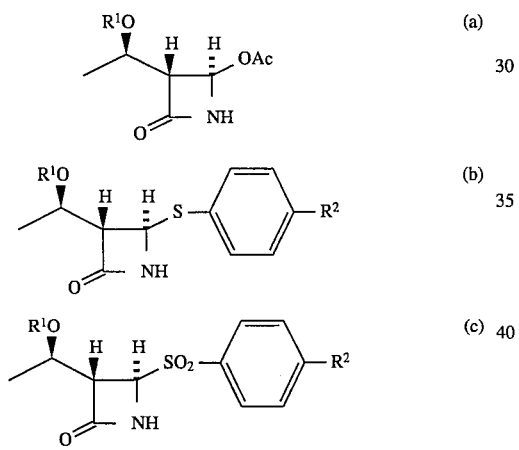

In the above formulas, $R^1$ and $R^2$ have the same definitions as mentioned above and OAc is acetoxy group.

DESCRIPTION OF THE PRIOR ART

The (E)-enolthioether derivatives of the said formula (IV) are the publicly known compounds and their manufacturing processes have been disclosed in some literatures. For example, a process of synthesizing (E)-enolthioether derivatives by five steps through the use of (R)-buten-1,3-diol as a starting material (J.C.S., Chem. Commun., Ishiguro et al., p 662, 1991), a process of synthesizing the same by six steps through the use of (R)-methyl-3-hydroxybutylate as a starting material (European Patent No. 179318/1986, Japanese Patent Laid-Open Gazette No. 207373/1986 and J. Antibiotics, Ishiguro et al., Vol. 41, p 1685, 1988), or the like are disclosed.

In particular, as to a preparation of (3R)-3-t-butyldimethylsilyloxy-1-(phenylthio)-1-butene, is disclosed a process comprising the following steps;

- first, (R)-buten-1,3-diol of formula (A) is reacted with p-toluenesulfonylchloride to obtain mono-p-toluenesulfonate of formula (B);
- the obtained compound (B) is treated with sodium benzenethiolate (NaSPh) to synthesize phenylsulfide compound of formula (C);
- the free secondary hydroxy group of the said compound is protected with t-butyldimethylsilyl group and then, its α-position is chlorinated by N-chlorosuccinimide;
- lastly, the said compound is dechlorinated in the presence of weak bases to obtain (E)-enolthioether derivatives of the following formula (D):

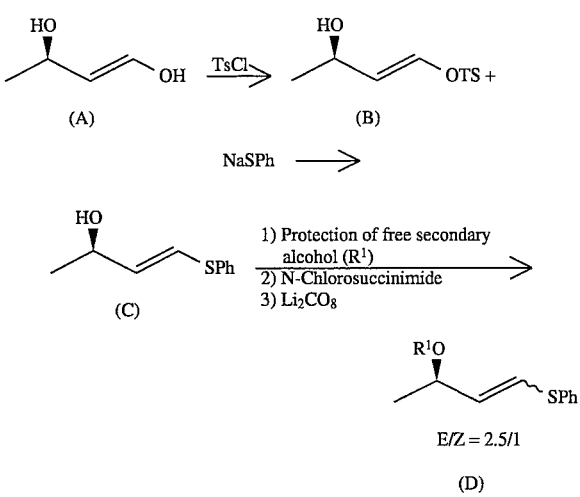

In the above formulas, $R^1$ has a same definition as mentioned above, and Ts is a p-toluenesulfonyl group.

Nevertheless, the manufacture of (E)-enolthioether derivatives of the said formula (D) based upon the aforementioned manufacturing processes has recognized the following disadvantages;

first, starting materials such as (R)-buten-1,3-diol and (R)-methyl-3-hydroxybutylate are high-priced compounds being obtained by the bio-organic transformation reaction;

second, the synthesizing steps are much longer and complicated;

third, the stereoselectivity of (E)-enolthioether derivatives of the said formula (D) is relatively low having the ratio of E(trans)/Z(cis) less than 2.5/1; and further improvements are still required.

SUMMARY OF THE INVENTION

Therefore, the inventors have intensively studied to overcome the aforementioned defects of the existing manufacturing methods, and as a result have completed the present invention by devising a process for manufacturing the objective (E)-enolthioether derivatives having high stereoselectivity through more simplified 3-step reaction than the existing methods, by using L-threonine as a starting material, a reasonable-priced α-amino acid being plentifully present in the nature.

DETAILED DESCRIPTION OF THE INVENTION

Namely, it is a principle object of the present invention to provide a process for manufacturing (E)-enolthioether derivatives (IV) stereoselectively, which comprises the steps;

a) the free secondary hydroxy group of L-threonine is silylated by trialkylsilyl chloride in the presence of 1,8-diazabicyclo[5,4,0]undec-7-ene and catalytic amount of substituted pyridine-type bases;

b) the α-amino acid part of the said silylated L-threonine derivative (I) is degraded by 1–4 equivalent of ninhydrin under the water-soluble organic solvent to prepare (2R)-2-(trialkylsilyloxy)propanal (II);

c) the Honor-Wordsworth-Emons (HWE) reaction between the resultant compound (II) and stabilized phosphonate ylide, phosphonium ylide or phosphine oxide ylide which was obtained by treating the organic phosphine compound (III) with strong base is carried out to obtain (E)-enolthioether derivative (IV).

The reaction scheme is shown below:

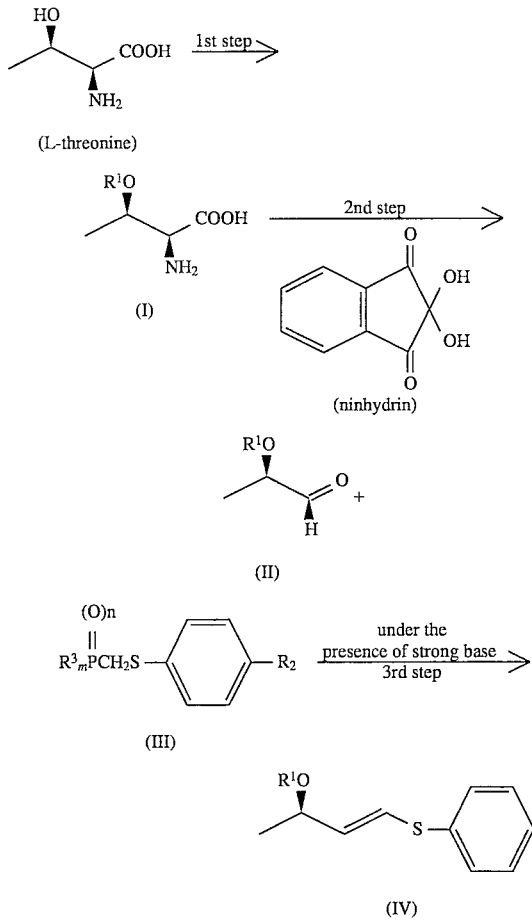

In the above formula, $R^1$ and $R^2$ have the same definitions as mentioned above, $R^3$ represents $C_{1-3}$ lower alkylalkoxy, allylalkoxy or allyl group; and m and n are integers of 2–3 and 0–1, respectively.

The first step of the present invention is to protect the free secondary hydroxy group of L-threonine with trialkylsilyl group. The manufacturing process of the compound of formula (I) is specified in a literature "Organic Preparation and Procedures INT., F. Orsini et al., Vol. 21, p 505, 1989", but the present invention has made it possible to shorten the reaction time and also to further improve the yield by using 0.1–0.3 equivalent of 4-dialkylaminopyridine, pyrrolidinopyridine, or piperidinopyridine and 1–1.5 equivalent of 1,8-diazabicyclo[5.4.0]undec-7-ene altogether.

The trialkylsilyl groups, which can be used in the said first step, include t-butyldimethylsilyl group, triisopropylsilyl group, isopropyldimethylsilyl group, isobutyldimethylsilyl group, 1,2-dimethylpropyldimethylsilyl group, dimethyl-1,2-trimethylpropylsilyl group, etc. Among them, t-butyldimethylsilyl group is the most stable during the reaction process.

The bases used in the first step include triethylamine, pyridine, N,N-tetramethylethylendiamine (TMEDA), diisopropylethylamine, 1,8-diazabicyclo[5.4.0]undec-7-ene, 1,5-diazabicyclo[4.3.0]-5-nonene, 1,4-diazabicyclo[2.2.0]octane, 2,6-rutinine, 4-dimethylaminopyridine, etc. Among them, the most favorable results were made by the concurrent use of 1,8-diazabicyclo[5.4.0]undec-7-ene with catalytic amount of 4-dimethylaminopyridine, pyrrolidinopyridine, or piperidinopyridine.

As a reaction solvent, inert organic solvents may be used. The "inert organic solvent" means an organic solvent which can dissolve all compounds used in the reaction and minimize the side reaction, but does not participate in the reaction or reduce the reactivity. The inert organic solvents include aromatic hydrocarbons such as benzene and toluene; ethers such as dioxane and tetrahydrofuran; halogenated hydrocarbons such as dichloromethane, 1,2-dichloroethane and chloroform; acetonitrile, N,N-dimethylformamide and N,N-dimethylacetamide. Among them, it is rather desirable to use acetonitrile as an inert organic solvent.

In order to reduce the side reactions, it is recommended to proceed the reaction step at a relatively low temperature, more desirably in 0° C. to room temperature and it is appropriate to determine the reaction time by 5 hours to 20 hours.

The second step of the present invention is to manufacture aldehyde by degrading the portion of α-amino acid, which is also called as "Strecker Degradation" (J. Am. Chem. Soc., W. S. Pones, Vol. 76, p 1337, 1954). In particular, this reaction stage is selectively implemented by ninhydrin, and the preferable amount of ninhydrin used is 1–4 equivalent. As a reaction solvent, water and/or alcohols (e.g. methanol, ethanol, isopropanol, etc.) may be used solely or in a mixture. It is rather desirable to use the mixture of water and methanol in an appropriate ratio.

In case that the reaction is to be conducted in a reflux temperature, the side reactions such as substrate decomposition may heavily occur. Thus, it is rather desirable to conduct the reaction at a temperature between room temperature and 60° C. Reaction time for the step is preferably 30 minutes to 4 burs.

The general manufacturing process of the second step comprises; first, L-threonine derivatives of the said formula (I) whose hydroxy group is protected with trialkylsilyl group, is dissolved in a mixture of water and methanol and then, 1.5 to 3 equivalent of ninhydrin dissolved in an appropriate amount of mixed solvent are added to the reacting solution at a time or in portions. The reaction is conducted in a temperature range from room temperature to 60° C. for 30 minutes to 2 hours by tracing with a thin layer chromatography. When the starting material is mostly or thoroughly disappeared, sodium chloride or saturated brine is added to the reaction mixture. After removing a dark-brown precipitate generated from the reaction through celite pad, the reaction mixture is extracted by organic solvent such as ethyl acetate, dichloromethane, chloroform or diethyl ether. Then, it is evaporated under reduced pressure to obtain the crude product, the aldehyde derivative. Said product is simply purified by a chromatography of short-column being filled with n-silica gel and finally, a relatively pure aldehyde derivative, which may be used in the next reaction as it is, is obtained in a high yield.

In the third step of the present invention, a derivative of the said formula (III) such as allylsulfide phosphonate, allylsulfide phosphine oxide or allylsulfide phosphonium derivatives are treated with a strong base to form a stabilized phosphonate ylide, phosphonium ylide or phosphine oxide ylide and then, the HWE reaction between the resultant phosphorus compound and the said aldehyde derivatives obtained from the said second step is carried out in the presence of an inert organic solvent to stereoselectively obtain the (E)-enolthioether derivatives of the said formula (IV). The amount of the said allylsulfide phosphonate, allylsulfide phosphine oxide or allylsulfide phosphonium derivatives which may be used as a substrate is preferably 1–2 equivalent and it is recommended to use tetrahydrofuran as a reaction solvent among the aforementioned inert organic solvent.

The following materials may be used as the strong base: sodium hydroxide, potassium hydroxide, sodium hydride, sodium alkoxide (NaOR: wherein R is a $C_{1-4}$ lower alkyl), sodium amide ($NaNH_2$), potassium amide ($KNH_2$), lithium diisopropylamide (LDA), n-butyl lithium (n-BuLi), etc. In particular, 1–2 equivalent of n-butyl lithium is preferable. It is recommended to conduct the reaction at the temperature range from room temperature to $-78°$ C., preferably $-10°$ C. to $-78°$ C., so as to obtain a sufficient yield of the objective compound (IV).

The aforementioned allylsulfide phosphonate, allylsulfide phosphine oxide or allylsulfide phosphonium derivatives are manufactured by referring to the publicly known processes (Syn. Commun., Blumenkof, Vol. 16, p 139, 1986 and J. Chem. Soc. Perkin Trans. I. S. Warren, et al., p 967, 1987). Various examples of the said derivatives are as follows:

- Dialkyl phosphonate derivatives such as dimethylphenylthiomethyl phosphonate, dimethyl-p-methylphenylthiomethyl phosphonate, dimethyl-p-methoxyphenylthiomethyl phosphonate, dimethyl-p-chlorophenylthiomethyl phosphonate, diethyl phenylthiomethyl phosphonate, diethyl-p-methylphenylthiomethyl phosphonate, diethyl-p-methoxyphenylthiomethyl phosphonate, diethyl-p-chlorophenylthiomethyl phosphonate, diisopropylphenylthiomethyl phosphonate, diisopropyl-p-methylphenylthiomethyl phosphonate, diisopropyl-p-methoxyphenylthiomethyl phosphonate, diisopropyl-p-chlorophenylthiomethyl phosphonate, diphenylphenylthiomethyl phosphonate, diphenyl-p-methylphenylthiomethyl phosphonate, diphenyl-p-methoxyphenylthiomethyl phosphonate, and diphenyl-p-chlorophenylthiomethyl phosphonate;

- Triaryl phosphonium derivatives such as phenylthiomethyltriphenyl phosphonium chloride and p-chlorophenylthiomethyltriphenyl phosphonium chloride;

- Diaryl phosphine oxide derivatives such as phenylthiomethyldiphenyl phosphine oxide, p-methylphenylthiomethyldiphenyl phosphine oxide, p-methoxyphenylthiomethyldiphenyl phosphine oxide and p-chlorophenylthiomethyldiphenyl phosphine oxide.

According to the present invention, (E)-enolthioether derivatives of the said formula (IV) may be obtained with better stereoselectivity and higher yield. The results are shown in Table 1.

TABLE 1

| m | n | $R^2$ | $R^3$ | trans(E)/cis(Z) | Yield of Compound (IV) (%) |
|---|---|---|---|---|---|
| 2 | 1 | H | OMe | 35.1/1 | 55 |
| 2 | 1 | OMe | OMe | 28/1 | 70 |
| 2 | 1 | Me | OMe | 40/1 | 65 |
| 2 | 1 | Cl | OMe | >50/1 | 68 |
| 2 | 1 | H | OEt | >100/1 | 82 |
| 2 | 1 | OMe | OEt | >100/1 | 80 |
| 2 | 1 | Me | OEt | >100/1 | 81 |
| 2 | 1 | Cl | OEt | >50/1 | 80 |
| 2 | 1 | H | O-i-Pr | all E | 70 |
| 2 | 1 | OMe | O-i-Pr | all E | 65 |
| 2 | 1 | Me | O-i-Pr | all E | 75 |
| 2 | 1 | Cl | O-i-Pr | all E | 73 |
| 2 | 1 | H | Ph | 9/1 | 61 |
| 2 | 1 | OMe | Ph | 35/1 | 44 |
| 2 | 1 | Me | Ph | 15/1 | 52 |
| 2 | 1 | Cl | Ph | 32/1 | 50 |
| 2 | 1 | H | OPh | all E | 74 |
| 2 | 1 | OMe | OPh | all E | 60 |
| 2 | 1 | Me | OPh | all E | 62 |
| 2 | 1 | Cl | OPh | all E | 65 |
| 3 | 0 | H | Ph | >20/1 | 63 |
| 3 | 0 | Cl | Ph | 15/1 | 54 |

As shown in the above Table, epimerism did not occur in the present invention, although it has been a general problem that the epimerism may occur in Wittig reaction of double bond in case that the α-position adjancent to the carbonyl functional group contains stereogenic center [Tetrahedron Lett., M. D. Sophor et al, pp 211, 1970 and J. Am. Chem. Soc., R. L. Soworvi et al, Vol. 94, pp 4758, 1972].

The progress of the said reaction was ascertained by a thin-layer chromatography, and the separation and more precise determination of the ratio of isomers was carried out by a high performance liquid chromatography. Each structure of E/Z-enolthioether derivatives of the said formula (IV), a final product, was ascertained by a proton nuclear magnetic resonance (NMR) spectrum. Further, after purifying the objective compound (IV) by a silica gel column chromatography, tris[3-(heptafluoropropylhydroxymethylene)-(−)-camphorate] Europhium (III), an optically active NMR shift reagent, was added to NMR solvents in an effort to ascertain the presence of any optical isomers and then, the optical rotatory intensity ($[\alpha]_D$) was measured.

As aforementioned, the present invention has characteristic advantages in comparison with the prior art in that the costs required for the process can be lowered because L-threonine, an α-amine acid of low in price is used as a starting material and the process is simple; and the desired (E)-enolthioether derivatives can be prepared with high stereoselectivity.

Now, the present invention is further illustrated referring to the following EXAMPLES, but it should not be understood that the present invention is delimited to the EXAMPLES.

EXAMPLE 1

Preparation of 0-t-butyldimethylsilyl-L-threonine

Under the nitrogen atmosphere, 50.0 g (0.42 mole) of L-threonine and 75.9 g (0.5 mole) of t-butyldimethylsilyl chloride were suspended in 500 ml of acetonitrile and then, the mixture was agitated at room temperature for 20 minutes. After lowering the reaction temperature to 0° C., 6.1 g (1.01 wt. %) of 4-dimethylaminopyridine and 83.73 g (0.55 mole) of 1,8-diazabicyclo[5.4.0]undec-7-ene were slowly added to the said mixture, and the resultant mixture was agitated at 0° C. for an hour. The reaction temperature increased slowly up to room temperature and then a strong agitation for 16 hours resulted white precipitate. By filtering the precipitate under reduced pressure, 81.67 g of the crude product was obtained. Meantime, the remaining solution after filtration was evaporated under reduced pressure to obtain white residue. The obtained residue was suspended to 200 ml of acetonitrile and strongly agitated at 0° C. for two hours to provide some white precipitate. Through the filtration, 11.6 g of the crude product was recovered. The combined crude product was crystallized from methanol/acetonitrile mixed solvent and filtered under reduced pressure to give 90.2 g (yield:92%) of white pure title compound.

$[\alpha]^{25}_D$ −28.2° (C=3.0, methanol; lit. −28.26°, C=2.9 in MeOH) $^1$H-NMR (CD$_3$OD) ; δ

0.10(s, 6H), 0.93(s, 9H), 1.30(d, 3H, J=6.5 Hz), 3.38(d, 1H, J=3.0 Hz), 4.65 (dq, 1H, J=6.5 Hz, 3.0 Hz) ppm.

EXAMPLE 2–10

Preparation of 0-t-butyldimethylsilyl-L-threonine

This EXAMPLE was conducted by using 1 equivalent of L-threonine and 1.2 equivalent of t-butyldimethylsilyl chloride as starting materials, while using 1.3 equivalent of 1,8-diazabicyclo[5.4.0]undec-7 -ene as the base. Under the conditions described in Table 2 as shown below, each different concentration of 4-dimethylaminopyridine, 4-pyrrolidinopyridine, or piperidinopyridine was used as the substituted pyridine base catalyst. The reaction was conducted in the same manner as did in EXAMPLE 1 to obtain the desired pure compounds. The reaction conditions and yield of the product are shown in the following Table 2.

TABLE 2

| Ex. | Reaction Solvent | Reaction Temp. (°C.) | Reaction Time (hr) | Conc. of Substituted pyridine | Yield (%) |
|---|---|---|---|---|---|
| 2 | CH$_3$CN | 25 | 24 | Dimethylaminopyridine (0.5) | 78 |
| 3 | CH$_3$CN | 25 | 24 | Dimethylaminopyridine (0.8) | 84 |
| 4 | CH$_3$CN | 25 | 16 | Dimethylaminopyridine (1.35) | 80 |
| 5 | DMF | 0 | 48 | Dimethylaminopyridine (1.01) | 65 |
| 6 | DMF | 25 | 24 | Dimethylaminopyridine (1.01) | 70 |
| 7 | CH$_3$CN | 25 | 48 | Pyrrolidinopyridine (1.01) | 65 |
| 8 | DMF | 25 | 24 | Pyrrolidinopyridine (1.01) | 60 |
| 9 | CH$_3$CN | 25 | 48 | Piperidinopyridine (1.01) | 55 |
| 10 | DMF | 25 | 48 | Piperidinopyridine (1.01) | 48 |

EXAMPLE 11

Preparation of (2R)-2-(t-butyldimethylsilyloxy)propanal 5 g (21.4 mmole) of 0-t-butyldimethylsilyl-L-threonine was dissolved in 150 ml of mixed solvent of distilled water and 2-propanol (2:1), and the mixture was heated to 60° C. A solution containing 7.63 g (42.8 mmole) of ninhydrin in 50 ml of 2-propanol was slowly dropped to the mixture, and the resultant mixture was agitated at 60° C. for 2.5 hours. Once the reaction was completed, the temperature was lowered to room temperature, and an excessive amount of sodium chloride was added to the mixture for saturation. After agitating vigorously, dark-brown precipitate was formed as a by-product. After removing the said dark-brown by-product by filtration, the remaining solution was extracted with 200 ml diethyl ether (100 ml ×2) and dried over anhydrous magnesium sulfate. By evaporating the organic solvent under reduced pressure, 3.6 g of the crude product was obtained.

3.6g of the the said crude product obtained therefrom was purified by a short-column chromatography (diethyl ether/n-hexane=⅕: containing 1% triethylamine), thereby obtaining 3 g of pure desired compound as a colorless oil (yield: 75%).

$^1$H-NMR (CDCl$_3$);

0.08(s, 6H), 0.91(s, 9H), 1.25(d, 3H, J=10 Hz), 4.22(m, 1H), 9.52(s, 1H, aldehyde-H) ppm

EXAMPLE 12

Preparation of (2R)-2-(t-butyldimethylsilyloxy)propanal

Under the nitrogen atmosphere, 5 g (21.4 mmole) 0-t-butyldimethylsilyl-L-threonine was dissolved in 100 ml of methanol. Then, the reaction temperature was raised up to 40° C., and a solution containing 6.86 g (38.5 mmole) of ninhydrin in 30 ml of methanol was slowly added to the said mixture. The resultant mixture was agitated at 40° C. to 45° C. for three hours. Once the reaction was completed, the temperature was lowered to 0° C., 60 ml of saturated brine was added to the mixture, and the resultant mixture was further agitated for 20 minutes. After removing the dark-brown reaction by-product by filtration, the remaining solution was extracted with 200 ml of diethyl ether (100 ml ×2), dried over anhydrous magnesium sulfate. By evaporating the organic solvent under reduced pressure, 4 g of the crude product was obtained.

Crude product obtained therefrom was purified in the same manner as did in the said EXAMPLE 12, thereby obtaining 3.4 g of pure desired compound as a colorless oil (yield: 84%).

EXAMPLE 13-31

Preparation of (2R)-2-(t-butyldimethylsilyloxy)propanal

These EXAMPLES were conducted by using 1 equivalent of 0-t-butyldimethylsilyl-L-threonine as starting material. Under the conditions described in Table 3 as shown below, each different concentration of ninhydrin was used as a degrading reagent of α-amino acid. In accordance with the EXAMPLE 11 and 12, the pure desired compound was obtained. The reaction conditions and yield of the product were shown in the following Table 3.

TABLE 3

| Ex. | Reaction Solvent | Reaction Temp. (°C.) | Reaction Time (hr) | Amount of ninhydrin used (equivalent) | Yield (%) |
|---|---|---|---|---|---|
| 13 | H$_2$O | reflux | 0.5 | 4 | 32 |
| 14 | H$_2$O | reflux | 1 | 3 | 40 |
| 15 | H$_2$O | reflux | 1 | 2 | 44 |
| 16 | H$_2$O | reflux | 2 | 1 | 23 |
| 17 | H$_2$O | 60 | 2.5 | 1.8 | 45 |
| 18 | H$_2$O | 60 | 2.5 | 2.5 | 52 |
| 19 | CH$_3$OH | reflux | 2 | 2.5 | 66 |
| 20 | CH$_3$OH | 60 | 3 | 2 | 72 |
| 21 | CH$_3$OH | 60 | 3 | 1.5 | 56 |
| 22 | CH$_3$OH | 40 | 3 | 2 | 77 |
| 23 | CH$_3$OH | 40 | 3 | 1.5 | 70 |
| 24 | CH$_3$OH | 25 | 8 | 2 | 41 |
| 25 | (CH$_3$)$_2$CHOH | reflux | 4 | 2 | 45 |
| 26 | (CH$_3$)$_2$CHOH | 40 | 8 | 2 | 55 |
| 27 | H$_2$O/CH$_3$OH(1/1) | 60 | 2.5 | 2 | 68 |
| 28 | H$_2$O/CH$_3$OH(1/2) | 60 | 2.5 | 2 | 72 |
| 29 | H$_2$O/CH$_3$OH(2/1) | 60 | 2.5 | 2 | 56 |
| 30 | H$_2$O/(CH$_3$)$_2$CHOH(2/1) | reflux | 2.5 | 2 | 55 |
| 31 | H$_2$O/(CH$_3$)$_2$CHOH(1/2) | 60 | 2.5 | 2 | 70 |

EXAMPLE 32

Stereoselective preparation of (E)-(3R)-3-t-butyldimethylsilyloxy-1-phenylthio-1-butene Method A:

Under the nitrogen atmosphere, 4.56 g (17 mmole) of diethylphenylthiomethyl phosphonate was dissolved in 50 ml of anhydrous tetrahydrofuran and after lowering the reaction temperature to −78° C., 10 ml (16 mmole) of 1.6M n-BuLi was added to the mixture over 10 minutes, and the resultant mixture agitated at the temperature of −78° C. for 30 minutes. At the same temperature, 3 g (16 mmole) of (2R)-2-(t-butyldimethylsilyloxy)propanal diluted with 15 ml of THF was added to the said reaction mixture, and after slowly increasing the reation temperature to 0° C., the mixture was stirred for another 1.5 hours. Once the reaction was completed, the reaction was quenched by adding saturated ammonium chloride solution. The solution was extracted by 150 ml of diethyl ether (50 ml ×3), dried over anhydrous magnesium sulfate, and evaporated under reduced pressure to obtain 4.5 g of the crude product.

4.5 g of the said crude product obtained therefrom was purified by a column chromatography (using n-hexane containing 1% diethyl ether as an eluent), thereby obtaining stereoselectively 3.8 g of desired compound having E/Z ratio of over 100/1 (yield: 75%).

Method B:

Under the nitrogen atmosphere, 4.56 g (17 mmole) of diethylphenylthiomethyl phosphonate was dissolved in 50 ml of anhydrous tetrahydrofuran and after lowering the reaction temperature to −45° C., 0.64 g (16 mmole) of NaH (60%) was added to the mixture at a time, and the reaction mixture was agitated at the temperature of −45° C. for 1 hour. At the same temperature, 3 g (16 mmole) of (2R)-2-(t-butyldimethylsilyloxy)propanal diluted with 15 ml of THF was added to the said mixture, and the reaction temperature slowly increased to 0° C., and the mixture agitated at 0° C. for another one hour. Once the reaction was completed, the reaction was quenched by adding saturated ammonium chloride solution. After the work-up treatment and purification in the same manner as did in the said method A, 2.5 g of desired compound having E/Z ratio of over 100/1 (yield: 54%) was stereoselectively obtained.

Method C:

Under the nitrogen atmosphere, 4.56 g (17 mmole) of diethylphenylthiomethyl phosphonate was dissolved in 50 ml of anhydrous tetrahydrofuran and after lowering the reaction temperature to −20° C., 1.41 g (16 mmole) of 95% t-BuOK was added to the mixture at a time. After agitating at the temperature of −20° C. for 1.5 hours, 3 g (16 mmole) of (2R)-2-(t-butyldimethylsilyloxy)propanal diluted with 15 ml of THF was added to the reaction mixture at the same temperature, and the reaction temperature slowly increased to 0° C., and then the mixture agitated at 0° C. for another three hours. Once the reaction was completed, the reaction was quenched by adding saturated ammonium chloride solution. After the work-up treatment and purification in the same manner as did in the said method A, 2.3 g of desired compound having E/Z ratio of over 100/1 (yield: 50%) was stereoselectively obtained.

(trans form)

$[1]_D^{25}$ −4.3° (C=1, CHCl$_3$)

$^1$H-NMR (CDCl$_3$) ; δ 0.06(6H, s), 0.89(9H, s), 1.22(3H, d, J=6.4 HZ), 4.34(1H, m), 5.86(1H, dd, J=5.3Hz, 15Hz), 6.31(1H, dd, J=1.4Hz, 15 Hz) 7.20–7.35(5H, m) ppm.

(cis form)

$^1$H-NMR (CDCl$_3$) ; δ 0.01 (6H, s), 0.83(9H, s), 1.16(3H, d, J=6.3 Hz), 4.73(1H, m), 5.75 (1 H, dd, J=8.1Hz, 9.5Hz), 6.10 (1 H, dd, J=0.7 Hz, 9.5Hz), 7.15–7.40(5H, m) ppm

EXAMPLE 33–44

Stereoselective preparation of
(E)-(3R)-3-t-butyldimethylsilyloxy-1-phenylthio-1-butene These EXAMPLES were conducted by using 1.1 equivalent of dimethylphenylthiomethyl phosphonate, diisopropylphenylthiomethyl phosphonate, diphenylphenylthiomethyl phosphonate or phenylthiomethyldiphenyl phosphine oxide as the starting materials. As shown in the following Table 4, a method selected from the methods of A, B, and C was conducted to form phosphonate ylide or phosphine oxide ylide, and in accordance with the process specified in EXAMPLE 32, the reaction was further conducted by the use of 1 equivalent of (2R)-2-(t-butyldimethylsilyloxy)propanal to obtain the desired compound stereoselectively. The synthetic methods of A, B, and C were the same as described in EXAMPLE 32. The E/Z ratio and yield of the product are described in the following table 4.

TABLE 4

| Example | R | Synthetic Method | E/Z ratio | Yield (%) |
|---|---|---|---|---|
| 33 | CH$_3$O | A | 35.1/1 | 67 |
| 34 | CH$_3$O | B | 20/1 | 50 |
| 35 | CH$_3$O | C | 15/1 | 38 |
| 36 | (CH$_3$)$_2$CHO | A | all E | 70 |
| 37 | (CH$_3$)$_2$CHO | B | all E | 48 |
| 38 | (CH$_3$)$_2$CHO | C | >100/1 | 40 |
| 39 | Ph | A | 9/1 | 61 |
| 40 | Ph | B | 9/1 | 55 |
| 41 | Ph | C | 8/1 | 50 |
| 42 | PhO | A | all E | 74 |
| 43 | PhO | B | all E | 60 |
| 44 | PhO | C | >100/1 | 50 |

EXAMPLE 45

Stereoselective preparation of
(E)-(3R)-3-t-butyldimethylsilyloxy-1-(p-methoxyphenylthio)-1-butene Under the nitrogen atmosphere, 3.24g (11 mmole) of diethyl-p-methoxyphenylthiomethyl phosphonate was dissolved in 50 ml of anhydrous tetrahydrofuran and after lowering the reaction temperature to −78° C., 6.87 ml (11 mmole) of 1.6M n-BuLi was added to the mixture for ten minutes. The resultant mixture was agitated at the temperature of −78° C. for 30 minutes. At the same temperature, 1.87 g (10 mmole) of (2R)-2-(t-butyldimethylsilyloxy)propanal diluted with 10 ml of anhydrous tetrahydrofuran was added to the said reaction mixture and the reaction temperature raised to 0° C., and then the mixture agitated at 0° C. for another 1.5 hours. Once the reaction was completed, the reaction was quenched by adding saturated ammonium chloride solution. After the work-up treatment in the same manner as did in method A of EXAMPLE 32, the crude product (2.92 g) obtained therefrom was purified by a column chromatography (using n-hexane containing 3% diethyl ether as an eluent), thereby 2.59 g of desired compound having E/Z ratio of over 100/1 (yield: 80%) was stereoselectively obtained.

(trans form)

$^1$H-NMR (CDCl$_3$) δ: 0.06(6H, s), 0.88(9H, s), 1.18(3H, d, J=6.4 Hz), 3.86(3H, s), 4.25(1H, m), 5.60(1H, dd,

J=5.4Hz, 14.7 Hz), 6.33(1H, dd, J=1.4, 14.7 Hz), 6.80–6.90 (2H, m), 7.25–7.35 (2H, m) ppm

EXAMPLE 46–49

Stereoselective preparation of
(E)-(3R)-3-t-butyl-dimethylsilyloxy-1-(p-methoxyphenylthio)-1-butene These EXAMPLES were conducted by using 1.1 equivalent of dimethyl-p-methoxyphenylmethyl phosphonate, diisopropyl-p-methoxyphenylmethyl phosphonate, diphenyl-p-methoxyphenylmethyl phosphonate or p-methoxyphenylthiomethyldiphenyl phosphine oxide as starting materials.

Under the conditions as described in the following Table 5, phosphonate ylide or phosphine oxide ylide was prepared and the reaction according to EXAMPLE 42 was conducted by the use of 1 equivalent of (2R)-2-(t-butyldimethylsilyloxy)propanal to obtain the desired compound stereoselectively. The reaction condition, E/Z ratio and yield of the product were described in the following Table 4.

TABLE 5

| Ex. | R | Reaction Solvent | Reaction Temp. (°C.) | Reaction Time (hr) | E/Z Ratio | Yield (%) |
|---|---|---|---|---|---|---|
| 46 | CH$_3$O | THF | −78→0 | 1.5 | 28/1 | 70 |
| 47 | (CH$_3$)$_2$CHO | THF | −78→0 | 2 | all E | 65 |
| 48 | PhO | THF | −78→0 | 2 | all E | 60 |
| 49 | Ph | THF | −78→0 | 2 | 35/1 | 44 |

EXAMPLE 50

Stereoselective preparation of
(E)-(3R)-t-butyldimethylsilyloxy-1-(p-chlorophenylthio)-1-butene Under the nitrogen atmosphere, 3.83 g (13 mmole) of diethyl-p-chlorophenylthiomethyl phosphonate was dissolved in 50ml of anhydrous tetrahydrofuran and after lowering the reaction temperature to −78° C., 7.5 ml (12 mmole) of 1.6M n-BuLi was added to the mixture over ten minutes, and then the resultant mixture was agitated at the temperature of −78° C. for 30 minutes. At the same temperature, 1.87 g (10 mmole) of (2R)-2-(t-butyldimethylsilyloxy)propanal diluted with 10 ml of anhydrous tetrahydrofuran was added to the said reaction mixture. After slowly raising the reaction temperature to 0° C., the reaction mixture was agitated at the same temperature for another one hour. Once the reaction was completed, the reaction was quenched by adding saturated ammonium chloride solution. After the work-up treatment in the same manner as did in the method A of EXAMPLE 32, 3.02 g of crude title compound was obtained. The crude product obtained was purified by a column chromatography (using n-hexane as an eluent), thereby obtaining stereoselectively 2.599 of desired compound having E/Z ratio of over 100/1 (yield: 80%).

(trans form)
$^1$H-NMR (CDCl$_3$) δ; 0.05(3H, s), 0.06(3H, s), 0.90(9H, s), 1.22(3H, d, J=6.6 Hz), 4.33 (1H, m), 5.85 (1H, dd, J=5.6Hz, 14.6Hz), 6.28 (1H, dd, J=1.1Hz, 14.6Hz), 6.90–7.30 (4H, m) ppm

EXAMPLE 51–54

Stereoselective preparation of
(E)-(3R)-3-t-butyldimethylsilyloxy-1-(p-chlorophenylthio)-1-butene These EXAMPLES were conducted by using 1.3 equivalent of dimethyl-p-chlorophenylmethyl phosphonate, diisopropyl-p-chlorophenylmethyl phosphonate, diphenyl-p-chlorophenylmethyl phosphonate or p-chlorophenylthiomethyldiphenyl phosphine oxide as the starting materials.

Under the conditions as described in the following Table 6, phosphonate ylide or phosphine oxide ylide was prepared and the reaction according to EXAMPLE 46 was further conducted by the use of −1 equivalent of (2R)-2-(t-butyldimethylsilyloxy)propanal to obtain the desired compound stereoselectively. The reaction condition, E/Z ratio and yield of the product are described in the following Table 6.

TABLE 6

| Ex. | R | Reaction Solvent | Reaction Temp. (°C.) | Reaction Time (hr) | E/Z Ratio | Yield (%) |
|---|---|---|---|---|---|---|
| 51 | CH$_3$O | THF | −78→0 | 1.5 | >50/1 | 68 |
| 52 | (CH$_3$)$_2$CHO | THF | −78→0 | 1.5 | all E | 73 |
| 53 | PhO | THF | −78→0 | 1.5 | all E | 65 |
| 54 | Ph | THF | −78→0 | 2 | 32/1 | 50 |

EXAMPLE 55

Stereoselective preparation of
(E)-(3R)-3-t-butyldimethylsilyloxy-1-(p-methylphenylthio)-1-butene Under the nitrogen atmosphere, 3.02 g (11 mmole) of diethyl-p-methylphenylthiomethyl phosphonate was dissolved in 50 ml of anhydrous tetrahydrofuran and after lowering the reaction temperature to −78° C., 6.25 ml (10 mmole) of 1.6M n-BuLi was added to the reaction mixture for ten minutes, and the resultant mixture was agitated at the temperature of −78° C. for 30 minutes. At the same temperature, 1.87 g (10 mmole) of (2R)-2-(t-butyldimethylsilyloxy)propanal diluted with 10 ml of anhydrous tetrahydrofuran was added to the said mixture and the reaction temperature was slowly raised from −78° C. to 0° C., and then the the mixture agitated at 0° C. for another one hour. Once the reaction was completed, the reaction was quenched by adding saturated ammonium chloride solution. After the work-up treatment in the same manner as did in method A of EXAMPLE 32, 2.8 g of crude product was obtained. The crude product was purified by a column chromatography (using n-hexane containing 1% diethyl ether as an eluent), thereby obtaining 2.5 g of desired compound having E/Z ratio of over 100/1 (yield: 81%) stereoselectively.

(trans form)

$^1$H-NMR (CDCl$_3$) ; δ0.06(6H, s), 0.90(9H, s), 0.21(3H, d, J=6.4 Hz), 2.35(3H, s), 4.33(1H, m), 5.78(1H, dd, J=5.5 Hz, 15.7 Hz), 6.35(1H, dd, J=1.5 Hz, 15.7 Hz), 7.05–7.25(4H, m) ppm

EXAMPLE 56–59

Stereoselective preparation of
(E)-(3R)-3-t-butyldimethylsilyloxy-1-(p-methylphenylthio)-1-butene These EXAMPLES were conducted by using 1.1 equivalent of dimethyl-p-methylphenylthiomethyl phosphonate, diisopropyl-p-methylphenyl phosphonate, diphenyl-p-methylphenylthiomethyl phosphonate or p-methylphenylthiomethyldiphenyl phosphine oxide as starting materials.

In the conditions as described in the following Table 7, phosphonate ylide or phosphine oxide ylide was formed, and then the reaction according to EXAMPLE 50 was further conducted by the use of 1 equivalent of (2R)-2-(t-butyldimethylsilyloxy)propanal to obtain the desired compound stereoselectively. The reaction condition, E/Z ratio and yield of the product are described in the following Table 7.

TABLE 7

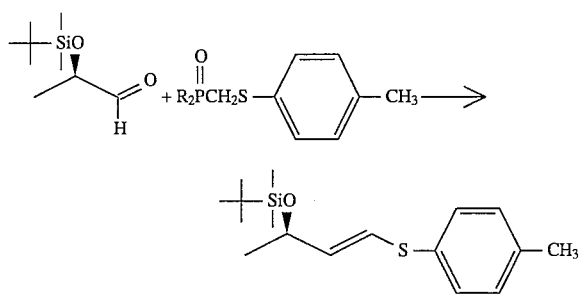

| Ex. | R | Reaction Solvent | Reaction Temp. (°C.) | Reaction Time (hr) | E/Z Ratio | Yield (%) |
|---|---|---|---|---|---|---|
| 56 | CH$_3$O | THF | −78→0 | 1.5 | 40/1 | 65 |
| 57 | (CH$_3$)$_2$CHO | THF | −78→0 | 1.5 | all E | 75 |
| 58 | PhO | THF | −78→0 | 1.5 | all E | 62 |
| 59 | Ph | THF | −78→0 | 3 | 15/1 | 52 |

EXAMPLE 60

Stereoselective preparation of
(E)-(3R)-3-t-butyldimethylsilyloxy-1-phenylthio-1-butene Under the nitrogen atmosphere, 7.15 g (17 mmole) of phenylthiomethyltriphenyl phosphonium chloride was dissolved in a mixture of 30 ml of anhydrous tetrahydrofuran and 15 ml of hexamethyl phosphoric triamide, and after lowering the reaction temperature to −78° C., 9.37 ml (15 mmole) of 1.6M n-BuLi was added to the mixture over ten minutes, and the mixture agitated at the temperature of −78° C. for one hour. At the same temperature, 1.87 g (10 mmole) of (2R)-2-(t-butyldimethylsilyloxy)propanal diluted with 10 ml of anhydrous tetrahydrofuran was added to the said mixture and the reaction temperature was slowly raised from −78° C. to −40° C. The mixture was agitated at −40° C. for six hours. Once the reaction was completed, the reaction was quenched by adding saturated ammonium chloride solution. After the work-up treatment and purification in the same manner as did in the method A of EXAMPLE 32, 1.94 g of desired compound having E/Z ratio of over 20/1 (yield: 63%) was obtained stereoselectively.

EXAMPLE 61

Stereoselective preparation of
(E)-(3R)-3-t-butyldimethylsilyloxy-1-(p-chlorophenylthio)-1-butene Under the nitrogen atmosphere, 7.74 g (17 mmole) of p-chlorophenylthiomethyltriphenyl phosphonium chloride was dissolved in a mixture of 30 ml of anhydrous tetrahydrofuran and 15 ml of hexamethyl phosphoric triamide, and after lowering the reaction temperature to −78° C., 9.37 ml (15 mmole) of 1.6M n-BuLi was added to the mixture over ten minutes. The resultant mixture was agitated at the temperature of −78° C. for one hour, and 1.87 g (10 mmole) of (2R)-2-(t-butyldimethylsilyloxy)propanal diluted with 10 ml of anhydrous tetrahydrofuran was added to the said mixture. The reaction temperature was slowly raised from −78° C. to 0° C., and agitated at 0° C. for four hours. Once the reaction was completed, the reaction was quenched by adding saturated ammonium chloride solution. After the work-up treatment and purification in the same manner as did in the method A of EXAMPLE 32, 1.74 g of desired compound having E/Z ratio of 15/1 (yield: 54%) was obtained stereoselectively.

We claim:

1. A process for stereoselective preparation of (E)-enalthioether derivatives comprising the steps of;
   (a) protecting free secondary hydroxy group of L-threonine with trialkylsilyl group; (b) the protected L-threonine derivatives (I) being degraded by ninhydrin to prepare (2R)-2-(trialkylsilyloxy)propanal (II); and (c) carring out the Honor-Wordsworth-Emons (HWE) reaction of the resultant compound (II) with stabilized phosphonate ylide, phosphonium ylide or phosphine oxide ylide which was obtained by treating the organic phosphine compound (III) with strong base to provide (E)-enolthioether derivatives(IV),

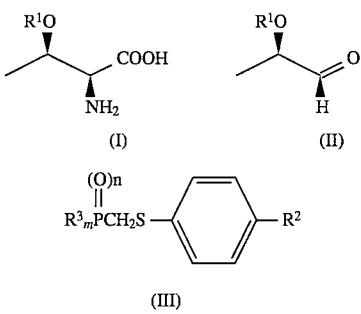

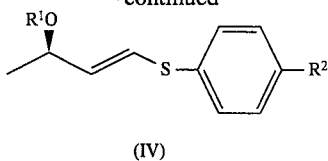

(IV)

in the above formulas, $R^1$ represents trialkylsilyl group; $R^2$ represents hydrogen, $C_{1-3}$ lower alkyl, $C_{1-3}$ lower alkoxy or halogen atom;

$R^3$ represents $C_{1-3}$ lower alkylalkoxy, allylalkoxy or allyl group; and m and n are integers of 2–3 and 0–1, respectively.

2. A process according to claim 1, wherein the protected trialkylsilyl group as a protective group is t-butyldimethylsilyl group.

3. A process according to claim 1, wherein the base selected from the group consisting of triethylamine, pyridine, N,N-tetramethylethylendiamine (TMEDA), diisopropylethylamine, 1,8-diazabicyclo[5.4.0]undec-7-ene, 1,5-diazabicyclo[4.3.0]-5-nonene, 1,4-diazabicyclo[2.2.0]octane, 2,6-rutinine, and 4-dimethylaminopyridine, together with catalyst selected from the group consisting of 4-dimethylaminopyridine, pyrrolidinopyridine, and piperidinopyridine were used in the process of protecting the free secondary hydroxy group of L-threonine.

4. A process according to claim 3, wherein the said base used in the process of protecting L-threonine is 1,8-diazabicyclo[5.4.0]undec -7-ene.

5. A process according to claim 1, wherein the reaction solvent in the manufacture of said formula (II) is selected from the group consisting of water, methanol, ethanol, 2-propanol and mixtures thereof.

6. A process according to claim 1, wherein the organic phosphorus compound represented by the said formula (III) is dialkyl phosphonate derivatives which are selected from the group consisting of dimethylphenylthiomethyl phosphonate, dimethyl-p-methoxyphenylthiomethyl phosphonate, dimethyl-p-methylphenylthiomethyl phosphonate, dimethyl-p-chlorophenylthiomethyl phosphonate, diethylphenylthiomethyl phosphonate, diethyl-p-methoxyphenylthiomethyl phosphonate, diethyl-p-methylphenylthiomethyl phosphonate, diethyl-p-chlorophenylthiomethyl phosphonate, diisopropylphenylthiomethyl phosphonate, diisopropyl-p-methoxyphenylthiomethyl phosphonate, diisopropyl-p-methylphenylthiomethyl phosphonate, diisopropyl-p-chlorophenylthiomethyl phosphonate, diphenylphenylthiomethyl phosphonate, diphenyl-p-methoxyphenylthiomethyl phosphonate, diphenyl-p-methylphenylthiomethyl phosphonate, and diphenyl-p-chlorophenylthiomethyl phosphonate.

7. A process according to claim 1, wherein the organic phosphorus compound represented by the said formula (III) is diaryl phosphine oxide derivative selected from the group consisting of diphenylphenylthiomethyl phosphine oxide, diphenyl-p-methoxyphenylthiomethyl phosphine oxide, diphenyl-p-methylphenylthiomethyl phosphine oxide and diphenyl-p-chlorophenylthiomethyl phosphine oxide.

8. A process according to claim 1, wherein the organic phosphorus compound represented by the said formula (III) is triaryl phosphonium derivative selected from the group consisting of phenylthiomethyltriphenyl phosphonium chloride and p-chlorophenylthiomethyltriphenyl phosphonium chloride.

9. A process according to claim 1, wherein strong bases selected from the group consisting of n-butyl lithium, potassium t-butoxide or sodium hydroxide is used and the reaction is conducted at a temperature below 0° C., in the step of treating the said organic phosphorus compound represented by the said formula (III) with strong base to obtain stabilized ylide.

10. A process according to claim 1, wherein the (E)-enolthioether derivatives represented by formula (IV) is selected from the group consisting of (E)-(3R)-3-t-butyldimethylsilyloxy-1-phenylthio-1-butene, (E)-(3R)-3-t-butyldimethylsilyloxy-1-(p-methoxyphenylthio)-1-butene, (E)-(3R)-3-t-butyldimethylsilyloxy-1-(p-chlorophenylthio)-1 butene and (E)-(3R)-3-t-butyldimethylsilyloxy-1-(p-methylphenylthio)-1 -butene.

* * * * *